United States Patent [19]

Browning

[11] Patent Number: 5,391,542
[45] Date of Patent: Feb. 21, 1995

[54] METHOD OF ENHANCING THE GROWTH OF PLANTS USING ALKYLOXYPOLYETHYLENEOXYETHANOLS

[76] Inventor: Henry A. Browning, Rte. 1, Box 90, Quitman, Ga. 31643

[21] Appl. No.: 74,457

[22] Filed: Jun. 10, 1993

[51] Int. Cl.$^6$ ............................................. A01N 31/02
[52] U.S. Cl. ................................................. 504/351
[58] Field of Search ............................... 504/351, 116

[56] References Cited

U.S. PATENT DOCUMENTS

| | | | |
|---|---|---|---|
| 4,096,661 | 6/1978 | Cleckner | 504/350 |
| 5,026,734 | 6/1991 | Browning | 514/723 |
| 5,141,963 | 8/1992 | Browning | 514/723 |
| 5,143,939 | 9/1992 | Browning | 514/723 |

OTHER PUBLICATIONS

Tergitol Publications: Overview and Product Information, Specialty Nonionic Curfactants: 15-S-9, 15-S-3, 15-S-5, 15-S-7, 15-S-20, 15-S-30, and 15-S-40 (1989) Union Carbide Chemicals and Plastics Co. Inc., Danbury, Conn.

*Primary Examiner*—Richard L. Raymond
*Assistant Examiner*—Brian G. Bambenick
*Attorney, Agent, or Firm*—Dowell & Dowell

[57] ABSTRACT

This invention relates to a method of enhancing the growth of plants. The method comprises applying a nonionic surfactant and, more particularly, an alkyoxypolyethyleneoxyethanol to the soil to protect the seeds and enhance their germination, and to enhance the growth of the plants. The nonionic surfactant is represented by the formula:

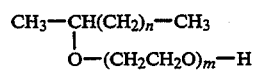

wherein n is from 9-15 and m is from 3-40. The nonionic surfactant can be combined with a substantially reduced rate of conventionally used pesticides to provide compositions that more effectively enhance plant growth than the conventional pesticides used alone at their full rates.

17 Claims, No Drawings

METHOD OF ENHANCING THE GROWTH OF PLANTS USING ALKYLOXYPOLYETHYLENEOXYETHANOLS

BACKGROUND OF THE INVENTION

1. Field of the Invention

This invention is a method of enhancing the growth of plants comprising applying a nonionic surfactant and, more particularly, an alkyoxypolyethyleneoxyethanol to soil to protect the plant seeds and enhance their germination, and to enhance the subsequent growth of the plants. The nonionic surfactant is represented by the formula:

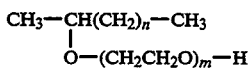

wherein n is from 9–15 and m is from 3–40.

2. Discussion of the Related Art

In U.S. Pat. No. 5,026,734 to Browning, the present inventor, discloses a method of controlling fungus, mites, termites, and other insect pests. In the disclosed method, a composition comprising a liquid carrier and at least one nonionic surfactant represented by the formula:

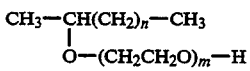

wherein n is from 9–15 and m is from 3–40 (hereinafter referred to as "the nonionic surfactant"), are applied to an infested location. The nonionic surfactant is the active ingredient of the applied composition. Browning discloses that not only does this particular surfactant effectively control insect pests, it also provides substantial environmental benefits over the prior used pesticides which have been found to include toxic pollutants that are injurious to plants, animals and thus the ecological balance. In contrast, the nonionic surfactant is biodegradable. Consequently, unlike the prior used pesticides, the nonionic surfactant can be safely applied without any subsequent monitoring to insure that it does not cause damaging effects.

A related U.S. Pat. No. 5,143,939 to Browning, discloses a method of treating soil and agricultural crops to control worms and nematodes. The method comprises applying the nonionic surfactant as the active ingredient to the infested soil and agricultural crops.

Finally, another related U.S. Pat. No. 5,141,963 to Browning, discloses a method of controlling ticks, mosquitoes and other insect pests by applying the nonionic surfactant as the active ingredient to an infested area.

The above mentioned patents to the present inventor have thus demonstrated that a particular nonionic surfactant can be used to effectively control a wide variety of insect pests when applied to infested soils and plants such as agricultural crops. These patents have further demonstrated that the nonionic surfactant can be applied to plants and soil without harming the plants, humans and other animals, or producing any adverse environmental effects.

The prior art has not recognized, however, that in addition to the nonionic surfactant being an extremely effective insecticide that is essentially harmless to plants, animals and the environment, the nonionic surfactant actually enhances the growth of plants.

The prior art further has not recognized that the nonionic surfactant can be used in combination with a significantly reduced rate of conventional pesticides to actually increase their plant growth enhancing effectiveness. Accordingly, the prior art has also failed to recognize that the known nonionic surfactant can substantially increase the cost effectiveness of the expensive conventional pesticides which can be applied at a substantially reduced rate. Furthermore, by combining the environmentally harmful conventional pesticides at a reduced rate with the nonionic surfactant, the resulting toxicity of the compositions can be substantially reduced.

SUMMARY OF THE INVENTION

The present invention has been made in view of the above inadequacies of the prior art and has as an object to provide a method of enhancing the growth of plants by applying to the soil a chemical that is essentially harmless to the plants when applied at proper rates, as well as to humans and other animals.

It is another object of the present invention to provide a method of enhancing the growth of plants by applying to the soil a chemical that is essentially harmless to the plants, in combination with a reduced rate of conventional pesticides, to produce compositions having increased growth enhancing properties and reduced toxicity.

To achieve the objects of the invention, as embodied and broadly described herein, the present invention comprises a method of enhancing the growth of plants, comprising applying to the soil an effective amount of a composition comprising a liquid carrier and at least one nonionic surfactant represented by the formula:

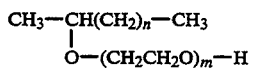

wherein n is from 9–15 and m is from 3–40

DETAILED DESCRIPTION OF THE PREFERRED EMBODIMENTS

The aforementioned alkyloxypolyethyleneoxyethanols are biodegradable nonionic surfactants consisting of a mixture of ethoxylates of secondary alcohols having from 9 to 15 carbon atoms in the aliphatic hydrophobic chain, and which have an average of 3 to 5, 7, 9, 12, 15, 20, 30 or 40 moles of ethylene oxide, respectively, in the hydrophilic entity. Materials having these compositions are available commercially as the TERGITOL 15-S series of ethylene oxide derivatives manufactured by the Union Carbide Corporation (i.e., 15-S-3, 15-S-5, 15-S-7, 15-S-9, 15-S-12, and 15-S-15). One method for the manufacture of such nonionic surface active agents is believed to be disclosed in U.S. Pat. No. 2,870,220. A blend or combination of these secondary alcohol ethoxylates such as TERGITOL 15-S-3 added to TERGITOL 15-S-9 are clear, easily handled materials for application. Of the available ethoxylates of secondary alcohols, TERGITOL 15-S-9 is preferred. As explained above, these nonionic surfactants can be represented by the formula:

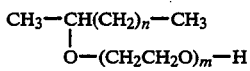

wherein n is form 9 to 15 and m is from 3 to 40.

Union Carbide characterizes the TERGITOL series with the empirical formula:

in its Material Safety Data Sheets.

The nonionic surfactants can be applied to targets such as seeds, plants, soils, etc. at a technical strength if desired. However, because of the active nature of the secondary alcohol ethoxylates, they are preferably admixed with a suitable carrier, especially when applied to targets such to plants, seeds and foliage. Suitable preferred inexpensive carriers are water or vegetable oil. The TERGITOL series are water soluble. Other more expensive carriers may optionally be used. In accordance with the present invention, the nonionic surfactants are preferably applied in an amount of approximately 8 oz. to about 32 oz. per acre. The corresponding amount of water or vegetable oil used as the carrier can vary considerably as long as a preferred amount of the nonionic surfactant is applied to the plants. Because vegetable oil forms a much finer mist than water, a substantially reduced volume of oil can be used with the nonionic surfactant as compared to the same amount of nonionic surfactant in water.

In recent laboratory testing, it has been unexpectedly discovered that TERGITOL 15-S-9 provides a number of previously unrecognized advantages. More particularly, it has been determined that when TERGITOL 15-S-9 is applied to soil, it protects plant seeds and enhances their germination. It is believed that this effect occurs because when it contacts the seeds, TERGITOL 15-S-9 forms a relatively fast drying seed covering that reduces the density of disease causing pathogens in the surrounding soil. Consequently, the germination seed experiences an early growth, and the plant stand and plant growth are improved.

After germination, plants that have been treated with TERGITOL 15-S-9 have had improved root systems in terms of their length and weight, improved shoot weight and plant height, and improved stand.

Moreover, it has also been determined in laboratory testing that by combining TERGITOL 15-S-9 with other conventional pesticides, the effectiveness of these other pesticides can be improved. More significantly, it has also been determined that by combining reduced rates of conventional pesticides with a relatively smaller amount of TERGITOL, the effectiveness of the conventional pesticides are improved even when they are used at substantially less than the manufacturers' recommended rates.

The following examples further illustrate preferred embodiments of the present invention. The examples are merely presented for the purpose of further illustrating the principles and previously unrecognized advantages of the present invention, and are not in any manner to be considered as limiting.

SEED PROTECTANT/GERMINATION ENHANCER

TERGITOL 15-S-9 was applied directly to cotton seed in the furrow at planting. The resulting germination and plant stand count data were as follows.

| Germination Results | |
|---|---|
| TERGITOL 15-S-9 Applied (pints) | Plants/10 seeds |
| 0 | 9 |
| 1 | 9.6 |
| 2 | 9.2 |
| 3 | 9.2 |
| Plant Stand Counts | |
| TERGITOL 15-S-9 Applied (pints) | Plants/Plot |
| 0 | 126.6 |
| 1 | 158.6 |

The above data clearly demonstrate the advantage of applying TERGITOL 15-S-9 to the soil to enhance the germination of plant seeds, and to improve the plant stand.

PLANT GROWTH ENHANCER

To demonstrate the effect of TERGITOL 15-S-9 on the enhanced growth of cotton seedlings in controlled greenhouse conditions, it was added directly to the soil. In the laboratory testing, DPL-20 cotton was used as the cultivar. The experimental design was a randomized complete block with four replications, and the plot design was two-pint styrofoam cups containing one seed each. For the chemical treatments, a control using water, and two different compositions containing 1 pint/acre and 2 pints/acre of TERGITOL 15-S-9 in water were used.

The soil used in laboratory testing was sterilized potting soil. By using this type of soil, potential result modifying factors including insect pests, nematodes and plant diseases were eliminated. Accordingly, the test results could be attributed with greater confidence to the effect of TERGITOL 15-S-9 on the growth of the cotton seedlings.

Moreover, by using sterilized soil, the test results could not be attributed solely to TERGITOL 15-S-9 destroying insect pests, nematodes and plant diseases caused by pathogens such as fungi, as it is capable of doing.

All of the treatments were subsequently examined with respect to phytotoxicity and plant stand, and the plant growth related parameters of fresh and dry root weights and shoot weights, root lengths, and plant heights were measured and recorded. The experimental results having a 95% confidence level were as shown in TABLE 1.

In TABLES 1 and 2, the reported data are the mean values of the four replications. The means were compared using Fisher's protected least significant difference (LSD) test.

TABLE 1

EFFECT OF SM-9 ON COTTON SEEDLING PLANT GROWTH IN THE GREENHOUSE

| Treatment | Rate (pint/acre) | Root Length (cm) | Root Weight (gm) Fresh | Dry |
|---|---|---|---|---|
| | | Five Days After Planting | | |
| 1. Control | — | 1.275 b | 0.030 b | 0.003 b |
| 2. TERGITOL | 1 | 5.250 a | 0.125 a | 0.014 a |

TABLE 1-continued

EFFECT OF SM-9 ON COTTON SEEDLING PLANT GROWTH IN THE GREENHOUSE

| Treatment | Rate (pint/acre) | Root Length (cm) | Root Weight (gm) | |
|---|---|---|---|---|
| | | | Fresh | Dry |
| 15-S-9 | | | | |
| 3. TERGITOL 15-S-9 | 2 | 5.075 a | 0.147 a | 0.015 a |
| LSD = 0.05 | | 2.024 | 0.056 | 0.011 |
| Six Days After Planting | | | | |
| 1. Control | — | 3.100 a | 0.096 b | 0.017 a |
| 2. TERGITOL 15-S-9 | 1 | 5.975 a | 0.121 b | 0.021 a |
| 3. TERGITOL 15-S-9 | 2 | 6.200 b | 0.164 a | 0.019 a |
| LSD = 0.05 | | 2.169 | 0.039 | 0.020 |
| Seven Days After Planting | | | | |
| 1. Control | — | 3.925 b | 0.096 b | 0.014 a |
| 2. TERGITOL 15-S-9 | 1 | 7.100 a | 0.123 a | 0.018 a |
| 3. TERGITOL 15-S-9 | 2 | 7.900 a | 0.137 a | 0.026 a |
| LSD = 0.05 | | 3.399 | 0.070 | 0.020 |
| Eight Days After Planting | | | | |
| 1. Control | — | 3.350 b | 0.065 b | 0.012 a |
| 2. TERGITOL 15-S-9 | 1 | 7.300 a | 0.163 ab | 0.014 a |
| 3. TERGITOL 15-S-9 | 2 | 7.100 a | 0.224 a | 0.016 a |
| LSD = 0.05 | | 2.170 | 0.126 | 0.009 |
| Nine Days After Planting | | | | |
| 1. Control | — | 3.750 b | 0.067 a | 0.008 a |
| 2. TERGITOL 15-S-9 | 1 | 5.225 a | 0.094 a | 0.016 a |
| 3. TERGITOL 15-S-9 | 2 | 6.550 a | 0.184 a | 0.016 a |
| LSD = 0.05 | | 5.447 | 0.137 | 0.015 |
| Ten Days After Planting | | | | |
| 1. Control | — | 3.425 b | 0.082 b | 0.028 a |
| 2. TERGITOL 15-S-9 | 1 | 8.457 a | 0.177 a | 0.021 a |
| 3. TERGITOL 15-S-9 | 2 | 5.356 a | 0.179 a | 0.028 a |
| LSD = 0.05 | | 2.823 | 0.082 | 0.033 |
| Eleven Days After Planting | | | | |
| 1. Control | — | 4.455 b | 0.074 b | 0.013 a |
| 2. TERGITOL 15-S-9 | 1 | 7.500 ab | 0.141 ab | 0.022 a |
| 3. TERGITOL 15-S-9 | 2 | 8.375 a | 0.192 a | 0.024 a |
| LSD = 0.05 | | 2.956 | 0.073 | 0.013 |
| Eighteen Days After Planting | | | | |
| 1. Control | — | 5.700 a | 0.236 a | 0.054 a |
| 2. TERGITOL 15-S-9 | 1 | 7.500 a | 0.396 a | 0.115 a |
| 3. TERGITOL 15-S-9 | 2 | 7.550 a | 0.304 a | 0.052 a |
| LSD = 0.05 | | 2.206 | 0.268 | 0.122 |
| Twenty-five Days After Planting | | | | |
| 1. Control | — | 16.850 b | 1.145 a | 0.165 b |
| 2. TERGITOL 15-S-9 | 1 | 23.425 a | 1.455 a | 0.228 a |
| 3. TERGITOL 15-S-9 | 2 | 17.950 ab | 1.433 a | 0.108 ab |
| LSD = 0.05 | | 6.396 | 0.576 | 0.118 |

As demonstrated by the above laboratory data, SM-9 significantly enhanced the growth of the cotton plants as compared to the untreated control for each period of time. For each group of data representing the different time periods, the root length and the root weight (either fresh or dry) were greater for the treated plants as compared to the controls. This result was demonstrated for treatments with one and two pints per acre rates of TERGITOL 15-S-9.

It is believed by the present inventor that the growth enhancing effect of TERGITOL 15-S-9 is caused by two different, but related, mechanisms. More particularly, it is believed that TERGITOL 15-S-9 increases: (1) the uptake of water by the plant, and (2) the absorption of nutrients from the soil into the plant. Because the nutrients are transported into the plant along with the water, when nutrients are present in the soil, the two mechanisms combine to provide a greatly improved intake of nutrients into the plant.

As shown by the data, TERGITOL 15-S-9 causes the plants to grow faster. When pathogens are present in the soil, TERGITOL 15-S-9 destroys them at the critical early growth stage so that the plants can experience a better early growth. By increasing the frequency of plants surviving this critical stage, TERGITOL 15-S-9 can directly increase plant stand.

The data also indicate that early plant growth can also be greatly improved in the absence of pathogens. More particularly, the data for five days after planting indicate that the root length and root weight were significantly higher for the seedlings treated with TERGITOL 15-S-9 as compared to the control. These data are believed to be due to an increased uptake of water by the treated plants.

To demonstrate that the growth enhancing effect of TERGITOL 15-S-9 is not limited to cotton plants, it was added directly to sterilized soil containing COKER-156 soybeans in further laboratory testing. The experimental design was again a randomized complete block with four replications, and the plot design was two-pint styrofoam cups containing one seed each. For the chemical treatments, a control using water and two different compositions containing 1 pint/acre and 2 pints/acre of TERGITOL 15-S-9 in water were used.

All treatments were subsequently examined with respect to phytotoxicity and plant stand, and the plant growth related parameters of fresh and dry root weights and shoot weights, root lengths, and plant heights were measured and recorded. The experimental results having a 95% confidence level were as shown in TABLE 2.

TABLE 2

EFFECT OF SM-9 ON SOYBEAN SEEDLING PLANT GROWTH IN THE GREENHOUSE

| Treatment | Rate (pint/acre) | Root Length (cm) | Root Weight (gm) | |
|---|---|---|---|---|
| | | | Fresh | Dry |
| Five Days After Planting | | | | |
| 1. Control | — | 4.947 a | 0.172 a | 0.045 a |
| 2. TERGITOL 15-S-9 | 1 | 5.777 a | 0.201 a | 0.041 a |
| 3. TERGITOL 15-S-9 | 2 | 7.500 a | 0.188 a | 0.050 a |
| LSD = 0.05 | | 5.037 | 0.087 | 0.029 |
| Six Days After Planting | | | | |
| 1. Control | — | 8.368 a | 0.343 a | 0.108 a |
| 2. TERGITOL 15-S-9 | 1 | 9.150 a | 0.371 a | 0.116 a |
| 3. TERGITOL 15-S-9 | 2 | 11.075 b | 0.376 a | 0.128 a |
| LSD = 0.05 | | 5.585 | 0.151 | 0.066 |
| Seven Days After Planting | | | | |
| 1. Control | — | 8.350 a | 0.297 a | 0.083 a |
| 2. TERGITOL 15-S-9 | 1 | 9.975 a | 0.696 ab | 0.248 a |
| 3. TERGITOL 15-S-9 | 2 | 11.750 a | 1.065 b | 0.486 a |

TABLE 2-continued
EFFECT OF SM-9 ON SOYBEAN SEEDLING PLANT GROWTH IN THE GREENHOUSE

| Treatment | Rate (pint/acre) | Root Length (cm) | Root Weight (gm) Fresh | Root Weight (gm) Dry |
|---|---|---|---|---|
| LSD = 0.05 | | 4.855 | 0.439 | 0.209 |
| Nine Days After Planting | | | | |
| 1. Control | — | 10.650 a | 0.773 a | 0.330 a |
| 2. TERGITOL 15-S-9 | 1 | 12.525 a | 1.159 a | 0.567 a |
| 3. TERGITOL 15-S-9 | 2 | 12.650 a | 1.076 a | 0.498 a |
| LSD = 0.05 | | 4.415 | 0.536 | 0.346 |
| Eleven Days After Planting | | | | |
| 1. Control | — | 12.900 a | 1.527 a | 0.595 a |
| 2. TERGITOL 15-S-9 | 1 | 12.500 a | 1.909 a | 0.383 a |
| 3. TERGITOL 15-S-9 | 2 | 14.325 a | 2.029 a | 0.524 a |
| LSD = 0.05 | | 3.496 | 0.799 | 0.263 |
| Eighteen Days After Planting | | | | |
| 1. Control | — | 9.450 a | 3.553 a | 0.763 a |
| 2. TERGITOL 15-S-9 | 1 | 10.805 a | 4.395 a | 1.008 a |
| 3. TERGITOL 15-S-9 | 2 | 11.850 a | 4.026 a | 1.158 a |
| LSD = 0.05 | | 4.682 | 1.086 | 0.263 |

The data for the soybean plants again demonstrate the enhanced plant growth for plants treated with TERGITOL 15-S-9.

Finally, to demonstrate that TERGITOL 15-S-9 can be combined with conventional pesticides for the purpose of increasing their effectiveness, and at the same time reducing the amount thereof that need be applied, TERGITOL 15-S-9 was added in relatively smaller amounts to a number of conventional pesticides, and the resulting compositions were applied to cotton seedlings. As a comparison, the full rates (i.e., the manufacturers' recommended rates) of the conventional pesticides were also applied to the soil. The subsequent growth of the plants in terms of the cotton stand, cotton height and cotton yield were later measured and recorded. The results were as shown in TABLE 3.

TABLE 3

| Cotton Stand | |
|---|---|
| Treatment/Rate | No. Cotton Plants/Plot |
| 1. TERRACHLOR SUPER X (full rate) | 124.4 |
| 2. TERRACHLOR SUPER X (½ rate) plus TERGITOL 15-S-9 (1 pint) | 127.6 |
| 3. RIDOMIL (full rate) | 125.2 |
| 4. RIDOMIL (½ rate) plus TERGITOL 15-S-9 (1 pint) | 129.2 |

| Cotton Height | |
|---|---|
| Treatment/Rate | Cotton Height (in.) |
| 1. TEMIK (7 lbs.) | 42.88 |
| 2. TEMIK (3.5 lbs.) plus TERGITOL 15-S-9 (1 pint) | 44.56 |
| 3. TERRACHLOR SUPER X (full rate) | 48.15 |
| 4. TERRACHLOR SUPER X (½ rate) plus TERGITOL 15-S-9 (1 pint) | 48.34 |
| 5. RIDOMIL (full rate) | 46.16 |
| 6. RIDOMIL (½ rate) plus TERGITOL 15-S-9 (1 pint) | 45.96 |

| Cotton Yield | |
|---|---|
| Treatment/Rate | Cotton Yield (lbs.) |
| 1. TERRACHLOR SUPER X (full rate) | 2914.13 |
| 2. TERRACHLOR SUPER X (½ rate) plus TERGITOL 15-S-9 (1 pint) | 2962.20 |
| 3. RIDOMIL (full rate) | 2191.72 |
| 4. RIDOMIL (½ rate) plus | 2643.67 |

TABLE 3-continued
TERGITOL 15-S-9 (1 pint)

The above data in TABLE 3 clearly demonstrate the previously unrecognized advantage of TERGITOL 15-S-9 as an additive to known pesticides to improve their effectiveness. For each different known pesticide and growth parameter, except for RIDOMIL and cotton height, the compositions containing a one-half rate of the pesticide plus one pint of TERGITOL 15-S-9 produced better results than the pesticides applied at a full rate. Furthermore, although not directly measured, the resulting toxicity of the compositions would be reduced as compared to the full rates of the pesticides due to the reduced volumes thereof that were applied.

The foregoing description of the preferred embodiment of the present invention has been presented to illustrate the principles of the invention and not to limit the invention to the particular embodiments illustrated. It is intended that the scope of the invention be defined by all of the embodiments encompassed within the following claims, and their equivalents.

What is claimed is:

1. A method of enhancing the growth of plants in soil, comprising applying to the soil an effective amount of a composition to enhance plant growth, said composition consisting essentially of a liquid carrier and at least one nonionic surfactant represented by the formula:

$$CH_3-CH(CH_2)_n-CH_3$$
$$|$$
$$O-(CH_2CH_2O)_m-H$$

wherein n is from 9-15 and m is from 3-40.

2. The method of claim 1, wherein said plants are cotton plants.

3. The method of claim 1, wherein said plants are soybean plants.

4. The method of claim 1, wherein said liquid carrier is comprised of water.

5. The method of claim 1, wherein said liquid carrier is comprised of vegetable oil.

6. The method of claim 1, wherein n is 15 and m is 9.

7. The method of claim 1, wherein said at least one nonionic surfactant is applied to the soil at a rate of at least one pint/acre.

8. The method of claim 7, wherein said at least one nonionic surfactant is applied to the soil at a rate of from about 1 pint/acre to about 2 pints/acre.

9. The method of claim 7, wherein n is 15 and m is 9.

10. A method of enhancing the growth of plants in soil, comprising applying to the soil an effective amount of a composition to enhance plant growth, said composition consisting essentially of a liquid carrier and at least one nonionic surfactant represented by the formula:

$$CH_3-CH(CH_2)_n-CH_3$$
$$|$$
$$O-(CH_2CH_2O)_m-H$$

wherein n is from 9-15 and m is from 3-40, and the nonionic surfactant is applied at a rate of at least approximately 8 ounces/acre.

11. A method of enhancing the germination of plant seeds in soil, comprising applying to the soil in which the seeds are planted an effective amount of a composition to enhance seed germination, said composition consisting essentially of a liquid carrier and at least one nonionic surfactant represented by the formula:

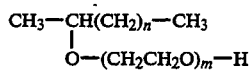

wherein n is from 9–15 and m is from 3–40.

12. The method of claim 11, wherein said liquid carrier is comprised of water.

13. The method of claim 11, wherein said liquid carrier is comprised of vegetable oil.

14. The method of claim 11 wherein n is 15 and m is 9.

15. The method of claim 11, wherein said at least one nonionic surfactant is applied to the soil at a rate of at least about one pint/acre.

16. The method of claim 13, wherein said at least one nonionic surfactant is applied to the soil at a rate of between about one pint/acre to two pints/acre.

17. The method of claim 15, wherein n is 15 and m is 9.

* * * * *